(12) United States Patent
Williams

(10) Patent No.: US 9,572,572 B2
(45) Date of Patent: Feb. 21, 2017

(54) CIRCULAR STAPLER MECHANICAL LOCKOUT

(71) Applicant: Covidien LP, Mansfield, MA (US)

(72) Inventor: Justin Williams, Naugatuck, CT (US)

(73) Assignee: COVIDIEN LP, Mansfield, MA (US)

(*) Notice: Subject to any disclaimer, the term of this patent is extended or adjusted under 35 U.S.C. 154(b) by 996 days.

(21) Appl. No.: 13/673,116

(22) Filed: Nov. 9, 2012

(65) Prior Publication Data

US 2014/0131417 A1    May 15, 2014

(51) Int. Cl.
| | | |
|---|---|---|
| *A61B 17/068* | (2006.01) | |
| *A61B 17/115* | (2006.01) | |
| *A61B 17/072* | (2006.01) | |

(52) U.S. Cl.
CPC ........ *A61B 17/068* (2013.01); *A61B 17/1155* (2013.01); *A61B 2017/07257* (2013.01); *A61B 2090/0814* (2016.02)

(58) Field of Classification Search
None
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 | 8/1972 |
| DE | 1057729 B | 5/1959 |

(Continued)

OTHER PUBLICATIONS

Extended European Search Report corresponding to European Application No. EP 13 19 2075.3, dated Mar. 19, 2014; 12191639.9, mailed Feb. 20, 2013; 9 pages.

*Primary Examiner* — Hemant M Desai
*Assistant Examiner* — Tanzim Imam

(57) ABSTRACT

A surgical stapling device is disclosed including a cartridge assembly and an anvil assembly. The anvil assembly is translatable relative to the cartridge assembly between a spaced position, where the anvil assembly is spaced from the cartridge assembly, and an approximated position, where the anvil assembly is in close cooperative alignment with the cartridge assembly for clamping tissue disposed therebetween. A lockout sleeve is slidably supported on the cartridge assembly and translatable relative to the cartridge assembly and the anvil assembly between a first position and a second position. The lockout sleeve is configured to engage the anvil assembly and the cartridge assembly when the lockout sleeve is in the second position to inhibit translation of the anvil assembly relative to the cartridge assembly from the spaced position to the approximated position.

15 Claims, 11 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,865,361 A | 2/1999 | Milliman et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | | |
|---|---|---|---|
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 * | 2/2008 | Aranyi ............... A61B 17/072 227/176.1 |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |

(56) References Cited

U.S. PATENT DOCUMENTS

| | | |
|---|---|---|
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0116009 A1* | 6/2005 | Milliman .......... A61B 17/068 227/176.1 |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0085034 A1* | 4/2006 | Bettuchi .......... A61B 17/115 606/219 |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065070 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |
| 2013/0181036 A1* | 7/2013 | Olson et al. ................ 227/180.1 |
| 2014/0008413 A1* | 1/2014 | Williams .......... A61B 17/1155 227/179.1 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2 682 061 A2 | 1/2014 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | WO 8706448 A | 11/1987 |
| WO | WO 8900406 A1 | 1/1989 |
| WO | WO 9006085 A1 | 6/1990 |
| WO | WO 01/54594 A1 | 8/2001 |
| WO | WO 2008/107918 A1 | 9/2008 |

* cited by examiner

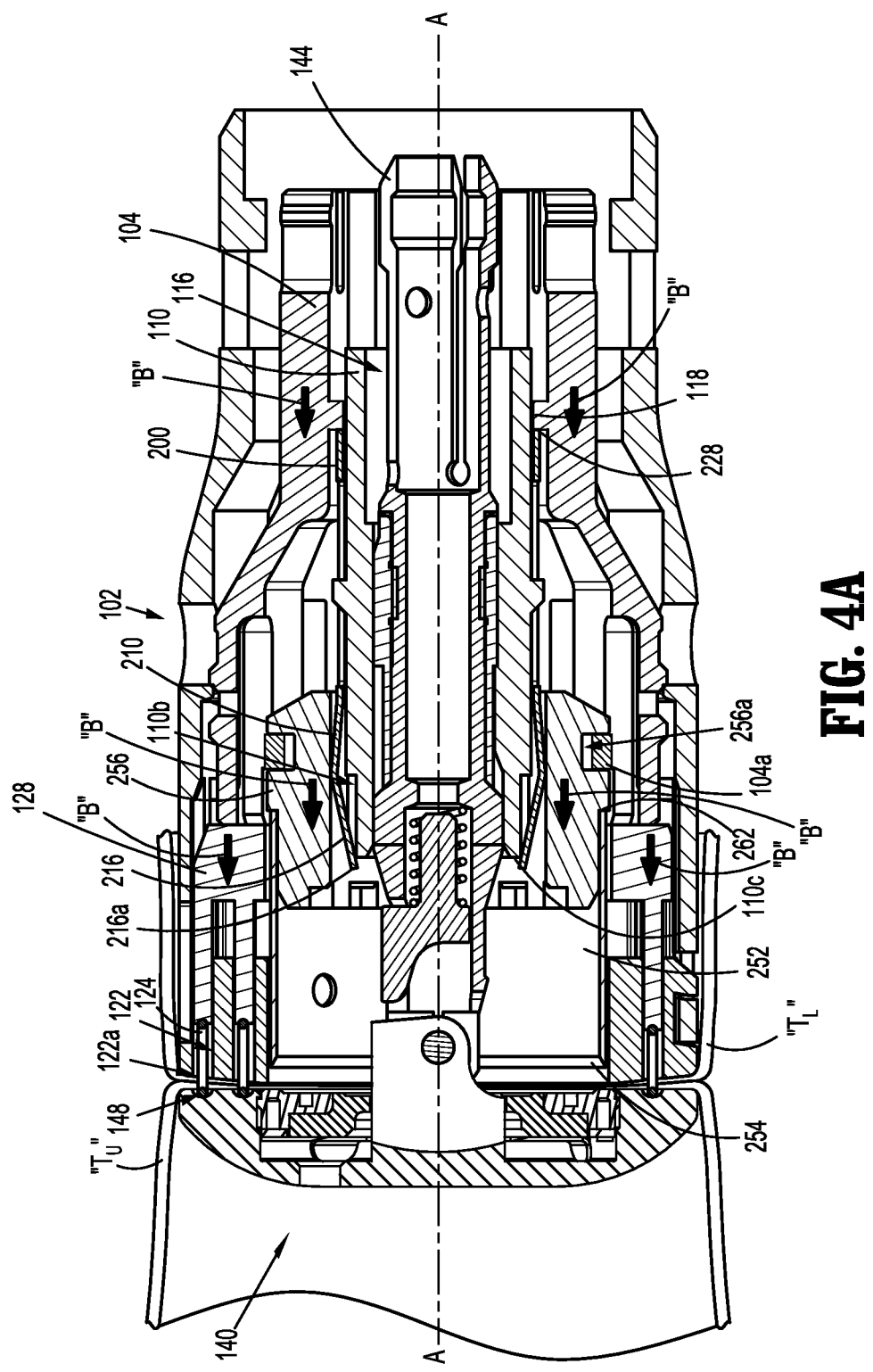

CIRCULAR STAPLER MECHANICAL LOCKOUT

BACKGROUND

Technical Field

The present disclosure relates to surgical instrumentation for performing a surgical procedure. More particularly, the present disclosure relates to circular stapling instruments and a lockout for inhibiting clamping of an anvil assembly after firing.

Background of Related Art

Circular staplers are known, as are their use in closed procedures, e.g., endoscopic procedures, laparoscopic procedures, or procedures through natural body orifices. Typically, circular staplers include a cartridge assembly on a distal end of an elongate body and an anvil assembly removably insertable into the cartridge assembly. The anvil assembly is approximated with the cartridge assembly to grasp tissue therebetween. The cartridge assembly includes a mechanism for forming staples against the anvil assembly and a knife for cutting the stapled tissue. Actuation of the anvil assembly and the cartridge assembly may be performed by a manually operated trigger or a powered drive assembly. Generally, both the actuation of the staple forming mechanism and the advancement of the knife occur at the same time, i.e., simultaneously. In an anastomosis procedure, the anvil assembly is first approximated relative to the cartridge assembly to grasp tissue therebetween and the cartridge assembly is then actuated by the trigger or powered drive to form the staples against the anvil assembly and to advance the knife to sever tissue. Typically, the cartridge assembly is only fired once and the anvil assembly is then un-approximated relative to the cartridge assembly. In some instances, however, a surgeon may attempt to re-approximate the anvil assembly relative to the cartridge assembly and fire the circular stapler again even though the staples of the cartridge assembly have already been exhausted.

SUMMARY

It would be beneficial to have a surgical stapling device which includes a lockout for inhibiting re-approximation of the anvil assembly with the cartridge assembly after the initial firing of the surgical stapling device. Accordingly, a surgical stapling device is provided which includes a lockout mechanism, e.g., a lockout sleeve which is configured to engage the anvil assembly and the cartridge assembly after firing to inhibit re-approximation of the anvil assembly relative to the cartridge assembly.

In an aspect of the present disclosure, a surgical stapling device for joining tissue portions is disclosed and includes a handle assembly, an elongate body extending from the handle assembly, a cartridge assembly supported on a distal end of the elongate body and including a staple cartridge containing a plurality of surgical staples in an annular array, and an anvil assembly at a distal end of the surgical stapling device having a shaft for removably coupling the anvil assembly to the cartridge assembly and a head pivotally mounted to a distal end of the shaft. The anvil assembly is translatable relative to the cartridge assembly between a spaced position, where the anvil assembly is spaced from the cartridge assembly, and an approximated position, where the anvil assembly is in close cooperative alignment with the cartridge assembly for clamping tissue disposed therebetween. The surgical stapling device further includes a lockout sleeve slidably supported on the cartridge assembly and translatable relative to the cartridge assembly and the anvil assembly between a first position and a second position. The lockout sleeve is configured to engage the anvil assembly and the cartridge assembly when the lockout sleeve is in the second position to inhibit translation of the anvil assembly relative to the cartridge assembly from the spaced position to the approximated position.

In an aspect of the present disclosure, the lockout sleeve includes at least one tab extending therefrom and configured to engage the anvil assembly when the lockout sleeve is in the second position to inhibit proximal translation of the anvil assembly relative to the lockout sleeve. The at least one tab may include a first portion substantially longitudinally aligned with the lockout sleeve and an inwardly biased leg extending from the first portion. The leg is configured to engage a flange of the anvil assembly to inhibit proximal translation of the anvil assembly relative to the lockout sleeve. The at least one tab may alternatively include a first portion substantially longitudinally aligned with the lockout sleeve, a second portion extending from the first portion substantially orthogonal to the first portion, and a leg extending from the second portion. The leg may be inwardly biased relative to the first and second portions. The at least one tab may extend from a distal end of the lockout sleeve.

In an aspect of the present disclosure, the cartridge assembly includes an inner cylindrical portion having at least one recess thereon. The at least one tab of the lockout sleeve may be disposed against the at least one recess when the lockout sleeve is in the first position.

In an aspect of the present disclosure, the lockout sleeve includes at least one hook extending therefrom and configured to engage the cartridge assembly when the lockout sleeve is in the second position to inhibit proximal translation of the lockout sleeve relative to the cartridge assembly. The at least one hook may be disposed adjacent a side wall of an inner cylindrical portion of the cartridge assembly when the lockout sleeve is in the first position and may be configured to snap over and engage an end of the inner cylindrical portion when the lockout sleeve is in the second position. The at least one hook may include a first portion extending from the lockout sleeve and substantially aligned with the lockout sleeve and an arcuate portion extending from the first portion. The arcuate portion may be configured to snap over and engage the end of the inner cylindrical portion of the cartridge assembly when the lockout sleeve is in the second position. The at least one hook may extend from a distal end of the lockout sleeve.

In an aspect of the present disclosure, the lockout sleeve includes a longitudinally extending slot configured for sliding reception of a tab of the cartridge assembly therein. The tab of the cartridge assembly is configured to engage a proximal end of the slot when the lockout sleeve is in the second position to inhibit distal translation of the lockout sleeve relative to the cartridge assembly beyond the second position.

In an aspect of the present disclosure, the cartridge assembly includes a drive member operably coupled to the handle assembly. The drive member is configured to engage the lockout sleeve to translate the lockout sleeve from the first position to the second position upon actuation of the handle assembly.

In an aspect of the present disclosure, the cartridge assembly includes a knife pusher operably coupled to the handle assembly and configured to distally advance a knife blade to sever tissue disposed radially inward of the staple cartridge upon actuation of the handle assembly.

In an aspect of the present disclosure, the cartridge assembly further includes a staple pusher operatively associated with the handle assembly and configured to drive the staples out of the cartridge assembly upon actuation of the handle assembly.

In an aspect of the present disclosure, a surgical stapling device for joining tissue portions is disclosed and includes a handle assembly, an elongate body extending from the handle assembly, and a cartridge assembly supported on a distal end of the elongate body. The cartridge assembly includes a staple cartridge containing a plurality of surgical staples in an annular array, a staple pusher configured for advancement through the staple cartridge to eject the plurality of surgical staples from the staple cartridge, a knife assembly configured for advancement through the cartridge assembly to sever tissue, and a drive member disposed within the cartridge assembly and in operative association with the handle assembly, the drive member configured to advance the staple pusher and the knife assembly upon actuation of the handle assembly. The surgical stapling device further includes an anvil assembly at a distal end of the surgical stapling device. The anvil assembly has a shaft for removably coupling the anvil assembly to the cartridge assembly and a head pivotally mounted to a distal end of the shaft. The anvil assembly is translatable relative to the cartridge assembly between a spaced position, where the anvil assembly is spaced from the cartridge assembly, and an approximated position, where the anvil assembly is in close cooperative alignment with the cartridge assembly for clamping tissue disposed therebetween. The surgical stapling device further includes a lockout sleeve slidably supported on the cartridge assembly and translatable relative to the cartridge assembly and the anvil assembly between a first position and a second position. The lockout sleeve is configured to engage the anvil assembly and the cartridge assembly when the lockout sleeve is in the second position to inhibit translation of the anvil assembly relative to the cartridge assembly from the spaced position to the approximated position.

In an aspect of the present disclosure, a method of locking out a surgical stapling device after firing is disclosed including translating an anvil assembly of the surgical stapling device from a spaced position, where the anvil assembly is spaced from a cartridge assembly of the surgical stapling device, to an approximated position, where the anvil assembly in close cooperative alignment with the cartridge assembly to clamp tissue therebetween, translating a staple pusher relative to the cartridge assembly to urge a plurality of fasteners disposed in the cartridge assembly through the tissue towards the anvil assembly, translating a lockout sleeve of the surgical stapling device relative to the cartridge assembly and the anvil assembly from a first position to a second position where a first portion of the lockout sleeve is disposed adjacent a shaft of the anvil assembly and a second portion of the lockout sleeve is engaged with the cartridge assembly to inhibit translation of the lockout sleeve from the second position to the first position, and translating the anvil assembly from the approximated position to the spaced position where the first portion of the lockout sleeve engages the anvil assembly to inhibit translation of the anvil sleeve from the spaced position to the approximated position.

In an aspect of the present disclosure, the first portion of the lockout sleeve may include a leg and the anvil assembly may include a flange. The leg of the lockout sleeve may engage the flange of the anvil assembly when the anvil assembly is translated from the approximated position to the spaced position to inhibit translation of the anvil assembly relative to the cartridge assembly from the spaced position to the approximated position.

In an aspect of the present disclosure, the second portion of the lockout sleeve may include a hook. The hook of the lockout sleeve may engage an inner cylindrical portion of the cartridge assembly when the lockout sleeve is translated from the first position to the second position to inhibit translation of the lockout sleeve from the second position to the first position.

In an aspect of the present disclosure, the method may further include translating a drive member of the cartridge assembly from a first condition to a second condition. The drive member may engage a proximal end of the lockout sleeve to translate the lockout sleeve from the first position to the second position.

In an aspect of the present disclosure, the drive member is operably coupled to a knife assembly slidably disposed in the cartridge assembly where translation of the drive member from the first condition to the second condition advances the knife assembly relative to the cartridge assembly to sever tissue disposed radially inward of the tissue clamped between the anvil assembly and the cartridge assembly.

Any of the above aspects of the present disclosure described may be combined with any other aspect of the present disclosure without departing from the scope of the present disclosure.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 4A is a side, cross-sectional view of the anvil and cartridge assemblies of FIG. 3, illustrating cartridge assembly during firing;

DETAILED DESCRIPTION OF EMBODIMENTS

Embodiments of the presently disclosed circular stapling instrument including a tilt-able anvil head will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
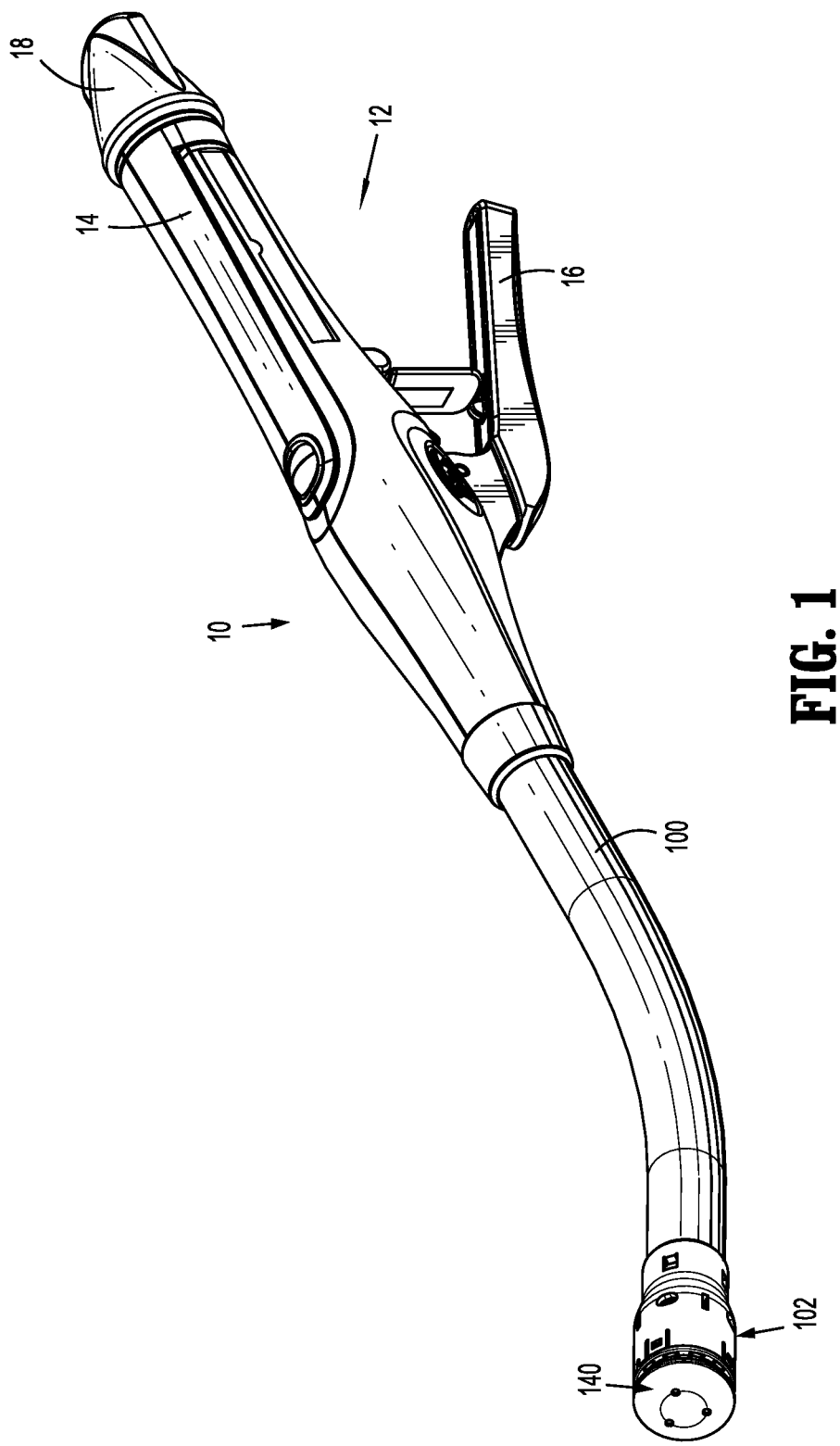
FIG. 1 is a perspective view of an exemplary circular stapler according to the present disclosure.

Referring initially to FIG. 1, a surgical stapling device, e.g., a circular stapler, is disclosed herein and is generally designated as circular stapler 10. Circular stapler 10 includes a handle assembly 12 and an elongate body 100 coupled to a distal end of handle assembly 12. A cartridge assembly 102 is mounted on a distal end of elongate body 100.

Handle assembly 12 includes a fixed handle 14 and a moveable handle or trigger 16. Handle assembly 12 also includes an adjustment knob 18 for moving anvil assembly 140 relative to cartridge assembly 102. The structure and function of handle assembly 12 will only be described herein to the extent necessary to fully disclose the operation of cartridge assembly 102. Examples of instruments for performing circular anastomosis of hollow organs are described in U.S. Pat. Nos. 6,053,390; 5,588,579; 5,119,987; 5,005,749; 4,646,745; 4,576,167; and 4,473,077, each of which is incorporated herein in its entirety by reference.

Elongate body 100 may extend from handle assembly 12 or may be removably attached to handle assembly 12 and may be constructed so as to have a curved shape along its length. It is contemplated that elongate body 100 may substantially rigid or may be flexible without departing from the scope of the present disclosure.

Handle assembly 12 may include a powered actuation mechanism configured to supply linear motion through elongate body 100 to cartridge assembly 102. For example, handle assembly 12 may include an electric motor or other electrical device (not shown) which produces rotational motion upon actuation of trigger 16 and converts the rotational motion into linear motion which is transmitted through elongate body 100 via a drive assembly (not shown) for use by cartridge assembly 102. It is contemplated that the motor or other electrical device may instead produce linear motion directly. Examples of instruments including powered actuation mechanisms for use with surgical stapling devices are described in co-pending U.S. patent application Ser. No. 12/946,082, filed Nov. 15, 2010, entitled "ADAPTERS FOR USE BETWEEN SURGICAL HANDLE ASSEMBLY AND SURGICAL END EFFECTOR" which is incorporated herein in its entirety by reference. It is also contemplated that the stapling device may have a replaceable head including the cartridge assembly, anvil member, and associated mechanisms. Such a stapling apparatus can include the manually actuated handle assembly of FIG. 1 and as described above, or can include a powered actuator assembly having first and second drive members. For example, U.S. patent application Ser. No. 12/946,082, noted above, discloses a surgical device having a powered actuator assembly. Such actuator assembly can be powered by a motorized handle.

Figure 3:
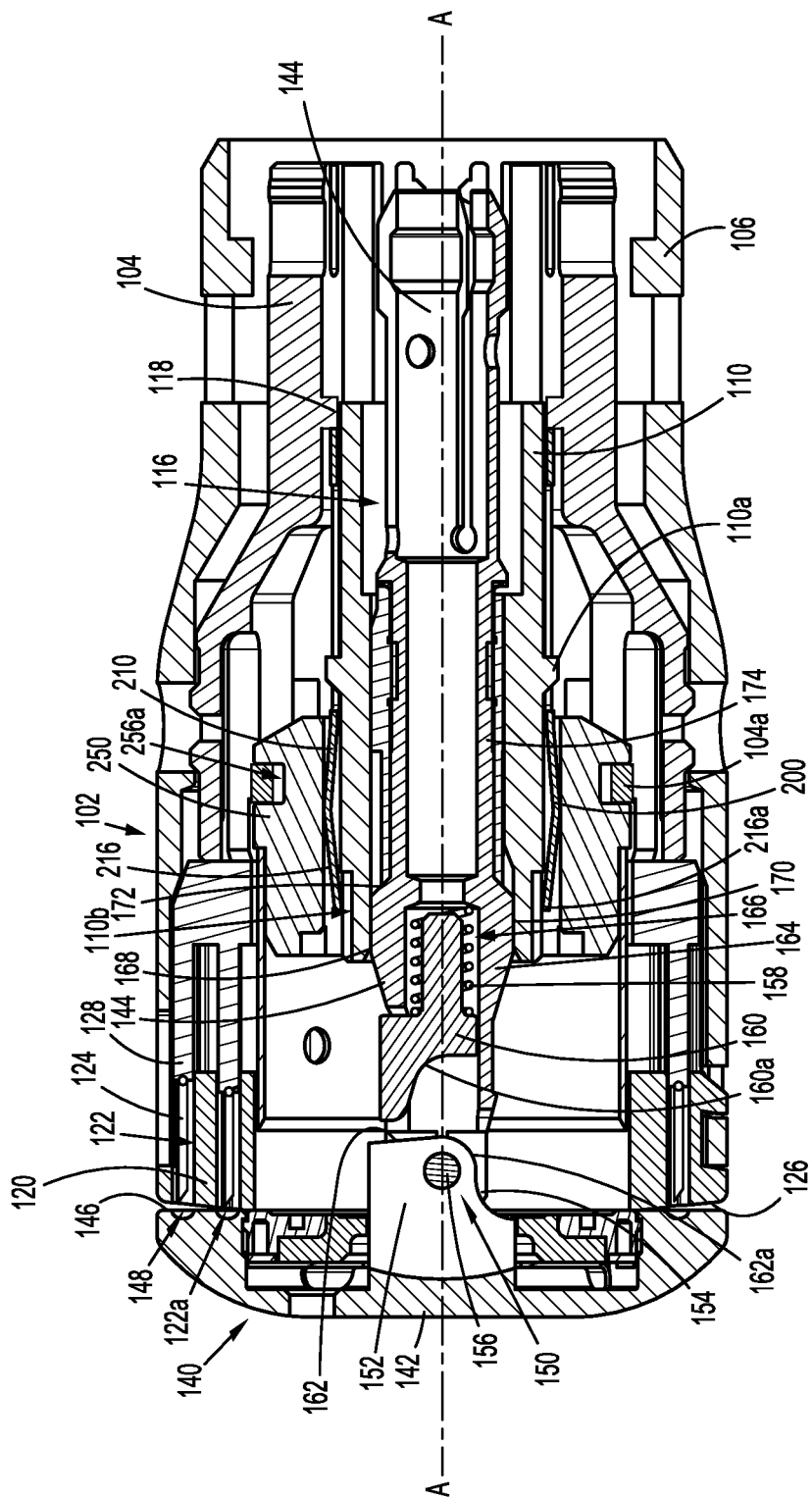
FIG. 3 is a side, cross-sectional view of the a cartridge assembly and an anvil assembly of the circular stapler of FIG. 1.

Cartridge assembly 102 defines a longitudinal axis A-A (FIG. 3). In one embodiment, cartridge assembly 102 is removably secured to elongate body 100 such that cartridge assembly 102 may be replaced and the circular stapler 10 may be reused. Alternatively, circular stapler 10 is configured for a single use, i.e., disposable.

Circular stapler 10 (FIG. 1) also includes an anvil assembly 140 positioned distally of cartridge assembly 102 and removably insertable into cartridge assembly 102. Anvil assembly 140 is translatable along longitudinal axis A-A (FIG. 3) relative to cartridge assembly 102.

Figure 4B:
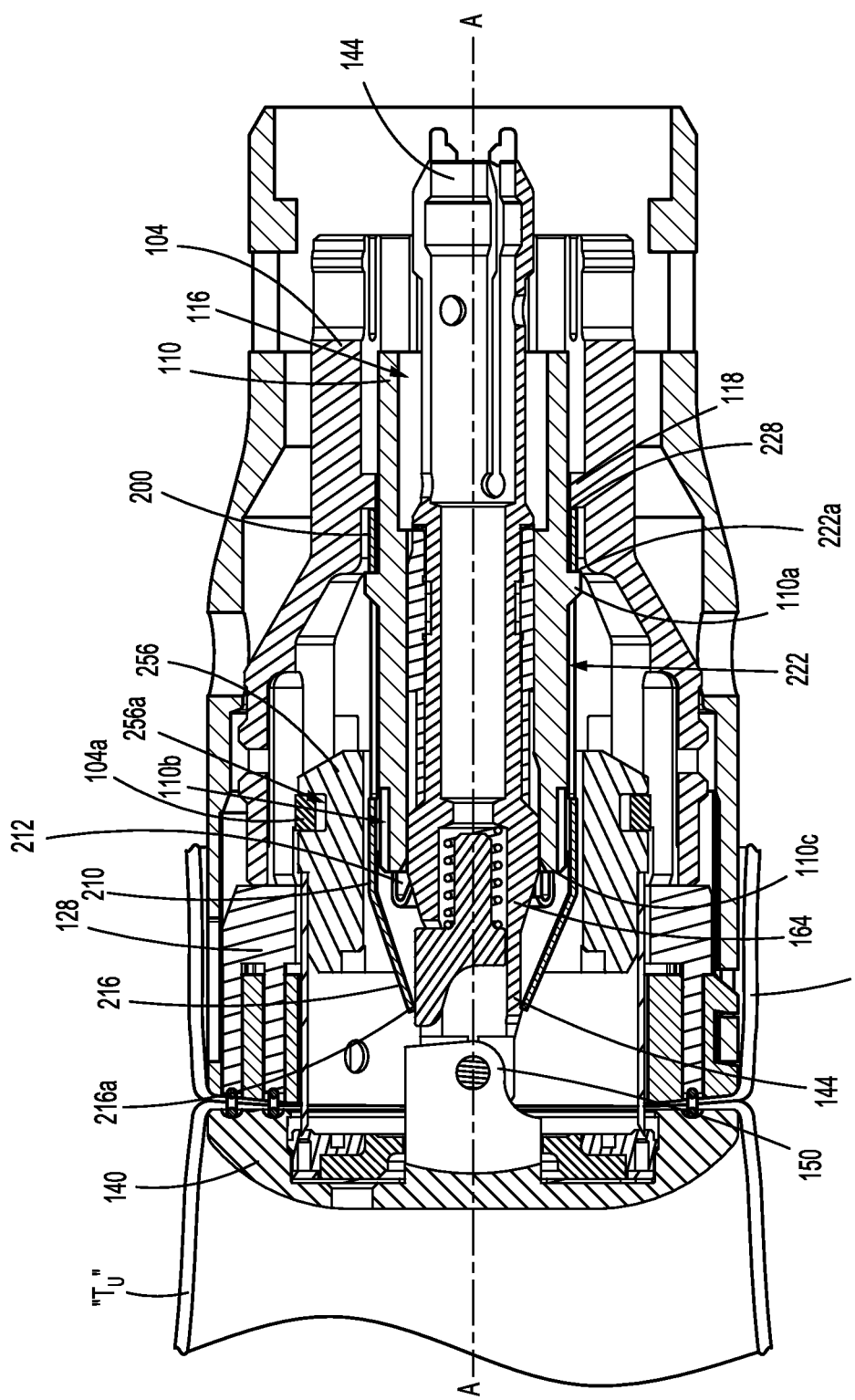
FIG. 4B is a side, cross-sectional view of the anvil and cartridge assemblies of FIG. 3, illustrating cartridge assembly after firing.
Figure 4C:
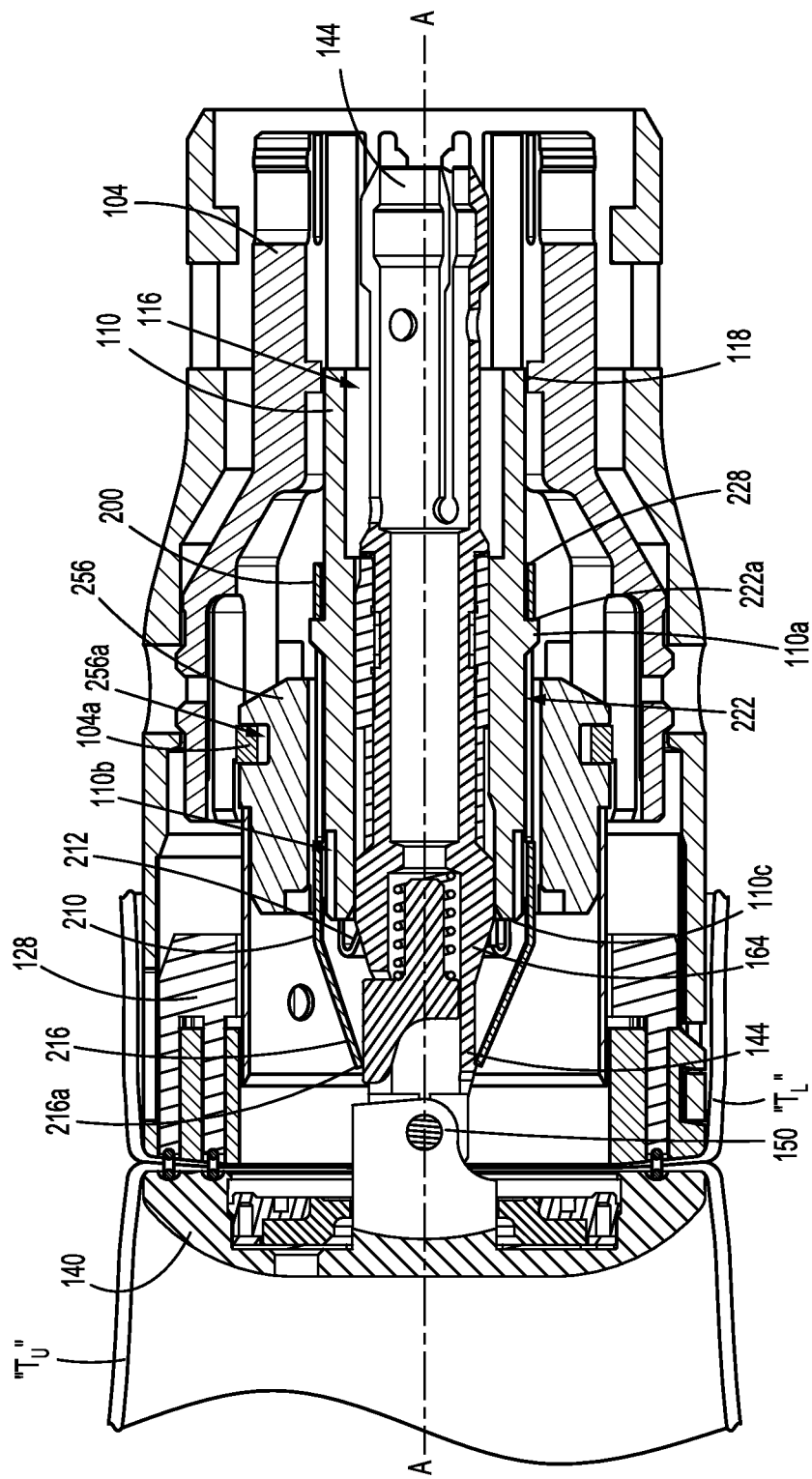
FIG. 4C is a side, cross-sectional view of the anvil and cartridge assemblies of FIG. 3, illustrating cartridge assembly after firing with the drive member returned to a proximal position.
Figure 5:
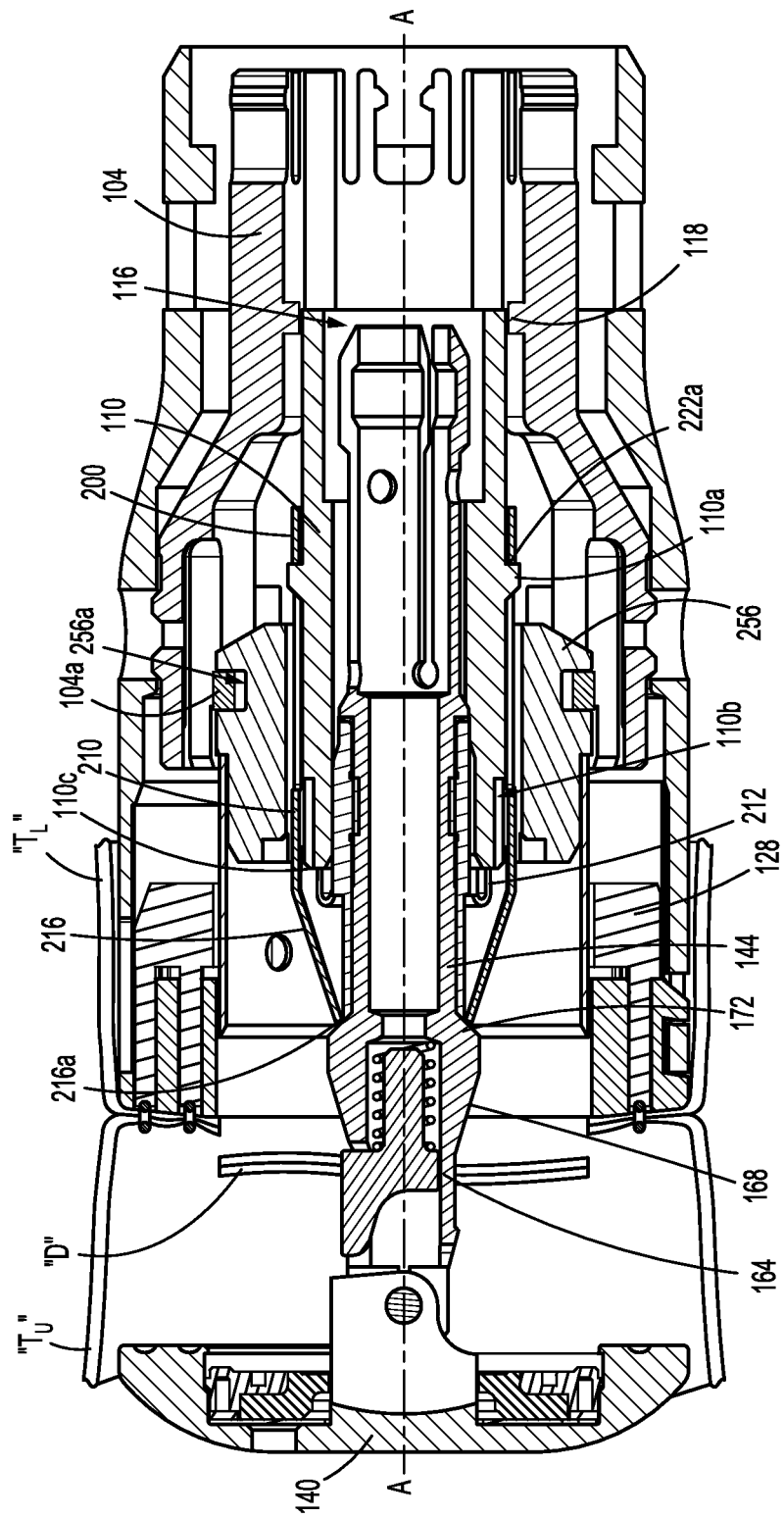
FIG. 5 is a side, cross-sectional view of the anvil and cartridge assemblies of FIG. 3, illustrating cartridge assembly after firing with the anvil assembly un-approximated relative to the cartridge assembly.

With reference now to FIGS. 3-5, anvil assembly 140 includes an anvil head 142 and an anvil shaft 144. Anvil shaft 144 is insertable into an inner bore 116 (FIGS. 6A and 6B) of cartridge assembly 102 and is removably and slidably securable within inner bore 116 of cartridge assembly 102. Shaft 144 is configured to be actuatable by handle assembly 12 (FIG. 1) to translate anvil assembly 140 axially along longitudinal axis A-A relative to cartridge assembly 102 to approximate or un-approximate anvil assembly 140 relative to cartridge assembly 102. For example, adjustment knob 18 (FIG. 1) may be actuated to translate anvil assembly 140 relative to cartridge assembly 102 to adjust the spacing between anvil head 142 and cartridge assembly 102.

Anvil head 142 includes a tissue contacting surface 146 defining staple forming pockets 148. Anvil head 142 is coupled to anvil shaft 144 by a pivot assembly 150 and is rotatable about pivot assembly 150 to tilt anvil head 142 from an un-tilted condition (FIG. 3) toward a tilted condition (not shown) for removal of circular stapler 10 from the body after a surgical stapling procedure is complete. In the un-tilted condition (FIG. 3), tissue contacting surface 146 of anvil head 142 is configured to be substantially perpendicular to longitudinal axis A-A. In the tilted condition (not shown) tissue contacting surface 146 of anvil head 142 is approximately aligned with or slightly offset relative to longitudinal axis A-A. For example, in the tilted condition (not shown), one portion of tissue contacting surface 146 may define an acute angle with longitudinal axis A-A while a remaining portion of tissue contacting surface 146 on an opposite side of shaft 144 may define an obtuse angle with longitudinal axis A-A.

Pivot assembly 150 includes an anvil base 152 of anvil head 142 and a distal end 154 of shaft 144. Distal end 154 of shaft 144 is inserted into anvil base 152 and rotatably secured therein by a pin 156. Anvil head 142 is spring biased toward the tilted condition by a spring 158 and a plunger 160 disposed in anvil shaft 144. Plunger 160 is configured to engage a proximal surface 162 of anvil head 142 adjacent or proximate to pivot assembly 150 and to urge anvil head 142 toward the tilted condition due to the bias of spring 158. Plunger 160 is also dimensioned to securely engage proximal surface 162 of anvil head 142 when anvil head 142 is in the tilted condition. For example, plunger 160 may include an annular surface 160a which is configured to engage a corresponding annular surface 162a of anvil head 142 to secure anvil head 142 in the final tilted condition.

With reference now to FIG. 3, anvil shaft 144 includes a spring housing 164 having an inner chamber 166 configured for the reception of spring 158 and at least a portion of plunger 160 therein and an outer surface 168 having a flange 170 and a tapered portion 172 extending from the flange 170 toward a proximal portion 174 of anvil shaft 144.

With reference now to FIGS. 3-6B, cartridge assembly 102 includes a drive member 104, a housing 106, a staple cartridge 120, a staple pusher 128, a knife assembly 250, and a lockout sleeve 200. Staple cartridge 120 is operably mounted at a distal end of cartridge assembly 102 and, in one embodiment, staple cartridge 120 is removably secured to cartridge assembly 102 such that staple cartridge 120 may be replaced.

Figure 6A:
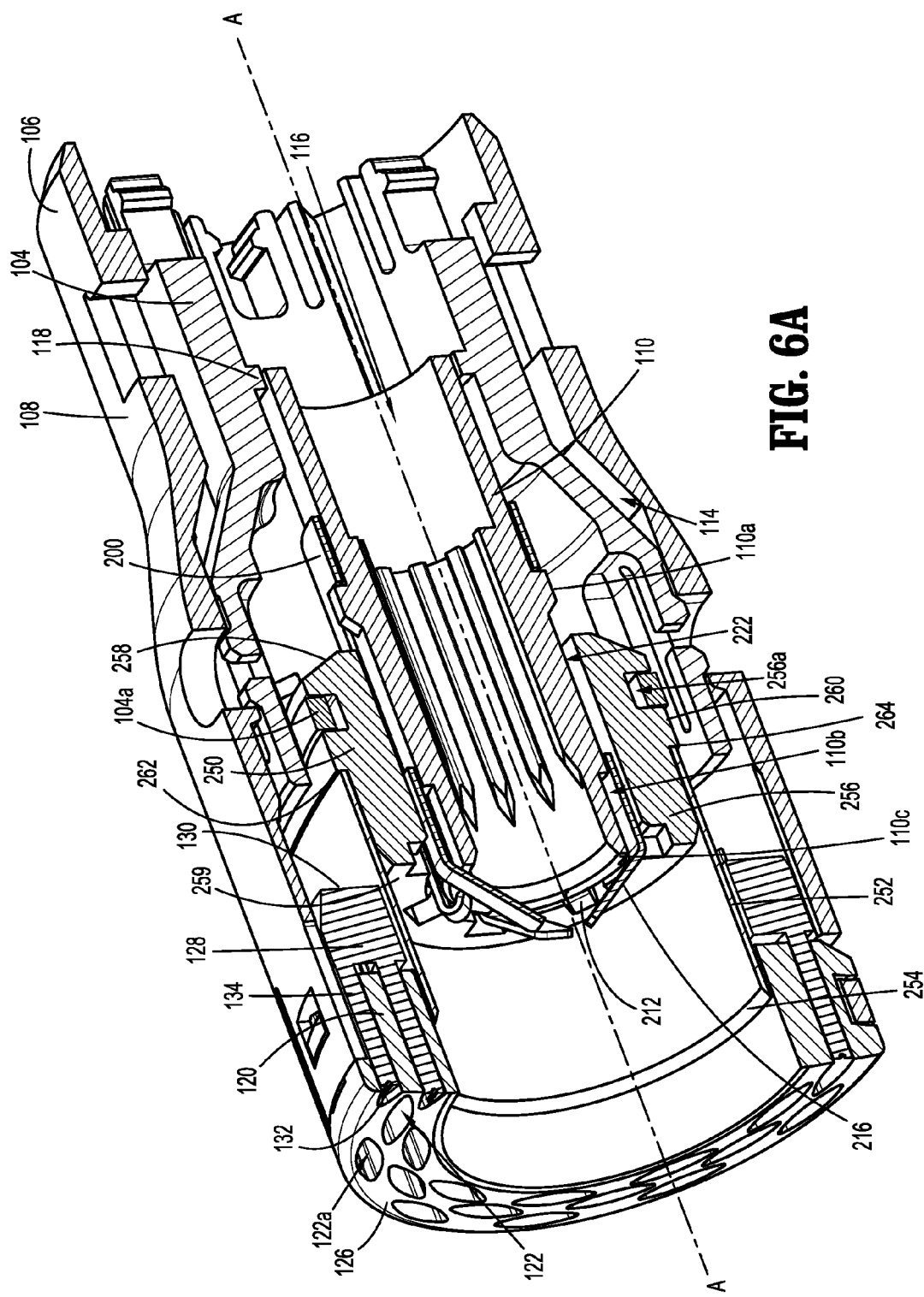
FIG. 6A is a perspective, longitudinal cross-sectional view of the cartridge assembly of FIG. 5, illustrating the lockout sleeve after firing engaged with an inner cylindrical portion of the cartridge assembly.
Figure 6B:
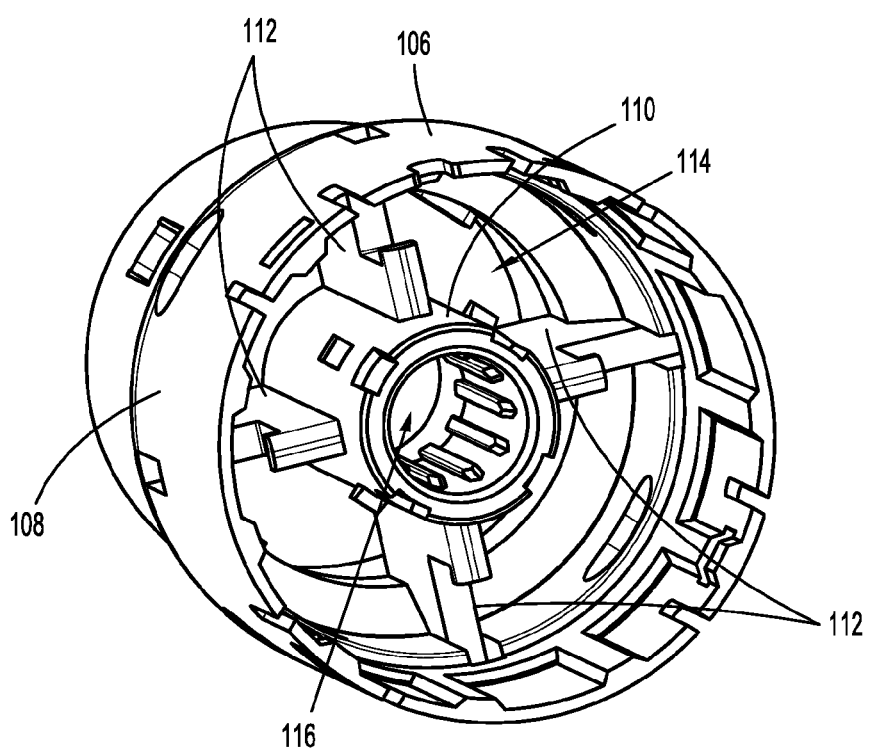
FIG. 6B is a front perspective view of an inner cylindrical portion and an outer cylindrical portion of the cartridge assembly of the circular stapler of FIG. 1, illustrating the inner and outer cylindrical portions joined by a plurality of ribs.

With reference now to FIGS. 6A and 6B, housing 106 of cartridge assembly 102 includes an outer cylindrical portion 108, an inner cylindrical portion 110, and a plurality of radially extending supports or ribs 112 extending between inner cylindrical portion 110 and outer cylindrical portion 108. Inner cylindrical portion 110 and outer cylindrical portion 108 of housing 106 are coaxial and define an annular channel 114 therebetween configured to receive staple pusher 128 and knife assembly 250. An inner bore 116 of cartridge assembly 102 extends through inner cylindrical portion 110 and is configured to receive shaft 144 of anvil assembly 140 therein for operable connection to adjustment knob 18 (FIG. 1).

Figure 2:
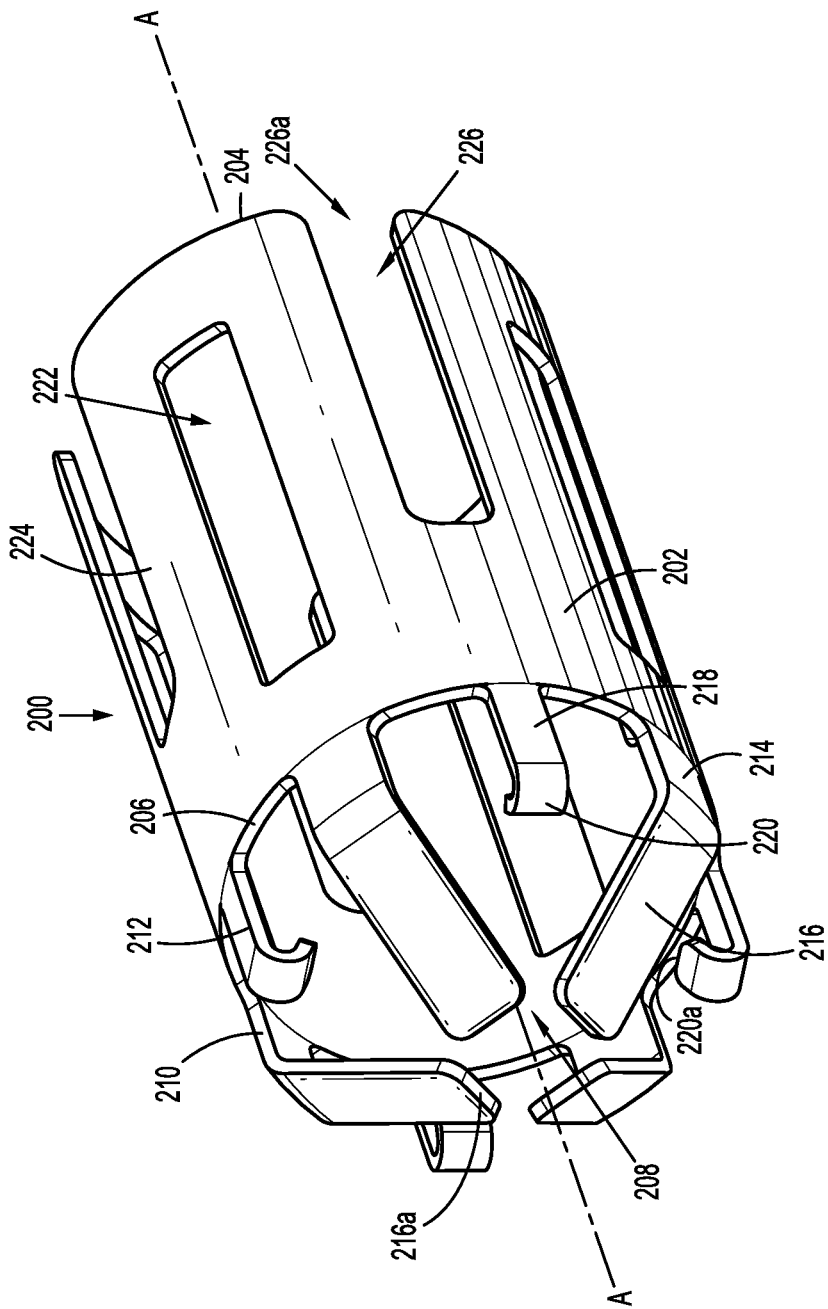
FIG. 2 is a perspective view of a lockout sleeve of the circular stapler of FIG. 1.

With reference now to FIG. 2, lockout sleeve 200 includes a substantially cylindrical housing 202 having a proximal end 204 and a distal end 206 and defining an inner bore 208 therethrough for the reception of inner cylindrical portion 110 (FIG. 6A) of housing 106 (FIG. 6A). A plurality of tabs 210 and a plurality of hooks 212 extend from distal end 206 of housing 202. Each tab 210 includes a longitudinal portion 214 extending distally from housing 202 and a leg 216 extending inwardly from the longitudinal portion 214 toward longitudinal axis A-A. Each leg 216 may be biased inward from longitudinal portion 214 toward the longitudinal axis A-A. Each hook 212 includes a longitudinal portion 218 extending distally from distal end 206 of housing 202 and an arcuate portion 220 extending from the longitudinal portion 218. Arcuate portion 220 curls inward relative to longitudinal portion towards axis A-A such that an end 220a is oriented in a generally proximal direction. For example, there may be four tabs 210 and four hooks 212 extending from distal end 206 of housing 202.

With reference now to FIGS. 2-6A, lockout sleeve 200 also includes a plurality of longitudinally extending slots 222 extending through a distal portion 224 of cylindrical housing 202. Each slot 222 is configured for sliding reception of a tab 110a of inner cylindrical portion 110 of inner housing 106. Each tab 110a of inner cylindrical portion 110 and corresponding slot 222 of lockout sleeve 200 allows lockout sleeve 200 to slide relative to housing 106 between a first, proximal position, where an end 216a of each leg 216 and the end 220a of each hook 212 is disposed against inner cylindrical portion 110, and a second, distal position, where the end 216a of each leg 216 and end 220a of each hook 212 is distal of the inner cylindrical portion 110. For example, each end 216a of each leg 216 may be disposed in a recess 110b extending proximally along inner cylindrical portion 110 from distal end 110c when lockout sleeve 200 is in the first, proximal position.

When lockout sleeve 200 is in the second, distal position, with anvil assembly 140 un-approximated, the end 216a of each leg 216 is inwardly biased into engagement with the tapered portion 172 of anvil shaft 144 to inhibit approximation of anvil assembly 140 relative to cartridge assembly 102 after firing of the surgical stapling device 10. The end 220a of each hook 212 engages a distal end 110c of inner cylindrical portion 110 to inhibit proximal advancement of lockout sleeve 200 relative to inner cylindrical portion 110. In this manner, approximation of anvil assembly 140 relative to cartridge assembly 102 after firing of the surgical stapling device 10 is inhibited. Lockout sleeve 200 also includes a plurality of slots 226 extending longitudinally from proximal end 204 of cylindrical housing 202 and configured for sliding reception of supports 112 (FIG. 6B) of housing 106 therethrough. Slots 226 extend through proximal end 204 of cylindrical housing 202 to define openings 226a for the reception of supports 112 (FIG. 6B). Drive member 104 includes a flange 118 for engagement with a proximal end 228 of lockout sleeve 200 during distal advancement of drive member 104 to urge lockout sleeve 200 distally from the first, proximal position to the second, distal position.

With reference now to FIGS. 3-6A, staple cartridge 120 includes at least one annular array of staple receiving slots 122 disposed at a distal end and a staple 124 disposed in each of staple receiving slots 122. For example, staple cartridge 120 may include one, two, or more than two annular arrays or rows of staple receiving slots 122. Staple receiving slots 122 include openings 122a extending through a tissue contacting surface 126 of the distal end of the staple cartridge 120. Staple cartridge 120 may be fixedly connected to the distal end of cartridge assembly 102 or may be configured to concentrically fit within the distal end of cartridge assembly 102.

With reference now to FIG. 6A, staple pusher 128 defines a substantially cylindrical shape and has a proximal portion 130 and a distal portion 132. Staple pusher 128 is coaxially and slidably disposed within channel 114, between outer cylindrical portion 108 and inner cylindrical portion 110. Distal portion 132 of staple pusher 128 defines a plurality of peripherally spaced fingers 134 in two concentric rows for engaging staples 124 within staple receiving slots 122. It is contemplated that one, two or more rows of fingers 134 may be included to correspond to the number of annular arrays of staple receiving slots 122 of staple cartridge 120. Each finger 134 of staple pusher 128 is received within one of the respective staple receiving slots 122 of staple cartridge 120 and is configured to translate through its respective staple receiving slot 122 and opening 122a during advancement of staple pusher 128 relative to cartridge assembly 102 to engage, drive and eject a respective staple 124 out of the opening 122a of the respective staple receiving slot 122, through tissue, and against a staple forming pocket 148 of anvil assembly 140 to thereby form staple 124. For example, staples 124 may be formed in a substantially B-shape.

With reference to FIGS. 3-6A, drive member 104 is slidably received within channel 114 of cartridge assembly 102 and is axially translatable within cartridge assembly 102 in response to actuation of trigger 16 (FIG. 1) of handle assembly 12 (FIG. 1). Drive member 104 is configured to engage a proximal portion or surface 130 of staple pusher 128 during axial translation, e.g. distal advancement, to advance staple pusher 128 axially through cartridge assembly 102 and staple receiving slots 122. Advancement of staple pusher 128 through staple receiving slots 122 urges staples 124 out of staple receiving slots 122 through openings 122a. Drive member 104 may alternatively be coupled to staple pusher 128 by, for example, snap fit, friction fit, or other similar methods of coupling. Drive member 104 and staple pusher 128 may alternatively be monolithically formed. In an embodiment, staple pusher 128 remains in a substantially advanced position after firing when drive member 104 is axially translated back, e.g., translated proximally, to an initial pre-fired position.

With reference now to FIGS. 3-6A, cartridge assembly 102 includes a knife assembly 250 slidably disposed in channel 114, radially inward of staple cartridge 120 and coaxially disposed about inner cylindrical portion 110 of housing 106. Knife assembly 250 is axially translatable along longitudinal axis A-A to sever a portion of the tissue disposed radially inward of staple cartridge 120 during actuation of circular stapler 10. Knife assembly 250 includes a knife blade 252 substantially in the form of an open cup or cylinder with the distal end thereof defining a knife edge 254.

As seen in FIGS. 3-6A, knife assembly 250 includes a knife pusher 256 having a proximal end surface 258 and a distal end surface 259. Knife pusher 256 is operatively coupled to drive member 104 by a tab 104a of drive member 104 disposed within with a slot 256a of knife pusher 256 such that distal or proximal advancement of drive member 104 causes distal or proximal advancement of knife pusher 256 along longitudinal axis A-A. Drive member 104 may be coupled to knife pusher 256 by, for example, snap fit, friction fit, or other similar methods of coupling. Drive member 104 and knife pusher 256 may alternatively be monolithically formed.

Knife pusher 256 includes a flanged portion 260 extending radially therefrom and defining a lip 262 thereon that is configured for engagement with a proximal end 264 of knife blade 252 during distal advancement of knife pusher 256. Knife pusher 256 may be coupled to knife blade 252 by a snap fit, friction fit, or other similar methods of coupling. Knife blade 252 and knife pusher 256 may alternatively be monolithically formed.

The operation of circular stapler 10 will now be described with reference to FIGS. 3-6A and 7. Referring initially to FIG. 3, cartridge assembly 102 is shown in an initial, or pre-fired condition, following approximation of anvil assembly 140 relative to cartridge assembly 102 from the spaced position to the approximated position in close cooperative alignment, with tissue "$T_U$" and "$T_L$" to be anastomosed disposed therebetween. In the initial condition, drive member 104, staple pusher 128, lockout sleeve 200, and knife pusher 256 are disposed in initial proximal positions with the legs 216 of lockout sleeve 200 disposed in the recesses 110b of inner cylindrical portion 110.

Prior to firing, shaft 144 of anvil assembly 140 is inserted through an upper portion of tissue "$T_U$", staple cartridge 120 is positioned against a lower portion of tissue "$T_L$" and shaft 144 is inserted through lower portion of tissue "$T_L$" into inner bore 116 of cartridge assembly 102. Anvil assembly 140 is then translated towards cartridge assembly 102 from the spaced position to the approximated position through actuation of knob 18 (FIG. 1) of handle assembly 12 (FIG. 1) to grasp or clamp the upper and lower portions of tissue "$T_U$" and "$T_L$" disposed therebetween. For clarity, upper and lower portions of tissue "$T_U$" and "$T_L$" will only be illustrated in the figures where necessary.

With reference now to FIGS. 4A-4C, during the firing of circular stapler 10 (FIG. 1), following approximation of anvil assembly 140 against staple cartridge 120, retraction or actuation of trigger 16 (FIG. 1) relative to handle 14 (FIG. 1) causes advancement of a drive assembly (not shown) which operably engages drive member 104 to cause advancement of drive member 104 in the direction indicated by arrows "B". As drive member 104 advances in the direction indicated by arrows "B", drive member 104 engages and drives staple pusher 128 in the direction indicated by arrows "B". As drive member 104 advances, drive member 104 also drives knife pusher 256 in the direction indicated by arrows "B" due to the coupling of tab 104a of drive member 104 with slot 256a of knife pusher 256. It is contemplated that the driving assemblies disclosed in the following U.S. patent applications can be used: Ser. No. 13/348,984, filed Jan. 12, 2012; Ser. No. 13/348,958, filed Jan. 12, 2012; and Ser. No. 13/365,372, filed Feb. 3, 2012, the disclosures of which are hereby incorporated by reference herein in their entirety.

As staple pusher 128 advances in the direction indicated by arrows "B", fingers 134 of staple pusher 128 advance through staple receiving slots 122 to drive or eject staples 124 out of staple receiving slots 122 through openings 122a, through tissue portions "$T_U$" and "$T_L$" grasped between anvil assembly 140 and staple cartridge 120, and against staple forming pockets 148 of anvil assembly 140 to thereby form staples 124. Staples 124 secure upper and lower tissue portions "$T_U$" and "$T_L$" together.

As knife pusher 256 advances in the direction indicated by arrows "B", knife blade 252 is also advanced distally due to lip 262 of flanged portion 260 engaging knife blade 252. As knife blade 252 is advanced distally, knife edge 254 engages and severs the portion of upper and lower tissue portions "$T_U$" and "$T_L$" (FIGS. 4A-4C) disposed radially inward of staple cartridge 120, thereby forming an anastomosis donut "D" (FIG. 5). The anastomosis donut "D" may be positioned coaxially about lockout sleeve 200 of anvil assembly 140. It is contemplated that the knife blade may be advanced with the staple pusher, or may be advanced in a separate stroke or actuation.

With reference again to FIGS. 4A-6A, as drive member 104 advances in the direction indicated by arrows "B", flange 118 of drive member 104 engages a proximal end 228 of lockout sleeve 200 and drives lockout sleeve 200 in the direction indicated by arrows "B" toward the second, distal, position. As lockout sleeve 200 is driven in the direction "B", the tabs 210 and hooks 212 of lockout sleeve 200 are driven distally of inner cylindrical portion 110 to release the legs 216 of lockout sleeve 200 from the recesses 110b. Once released, the legs 216 of lockout sleeve 200 are positioned against anvil shaft 144, e.g., against pivot assembly 150 or spring housing 164, and hooks 212 of lockout sleeve 200 snap over and engage distal end 110c of inner cylindrical portion 110 to inhibit proximal advancement of lockout sleeve 200 relative to inner cylindrical portion 110. Further distal advancement of lockout sleeve 200 is inhibited by tabs 110a of inner cylindrical portion 110 engaging the proximal ends 222a of slots 222. Lockout sleeve 200 is now locked in the second, distal position.

With reference now to FIGS. 4B and 4C, once lockout sleeve 200 is locked in the second, distal position, drive member 104 is retracted. As drive member 104 retracts, knife pusher 256 is also retracted proximally to the initial position due to the coupling of tab 104a of drive member 104 with the slot 256a of knife pusher 256. Staple pusher 128 remains at least partially in the advanced position.

Figure 7:
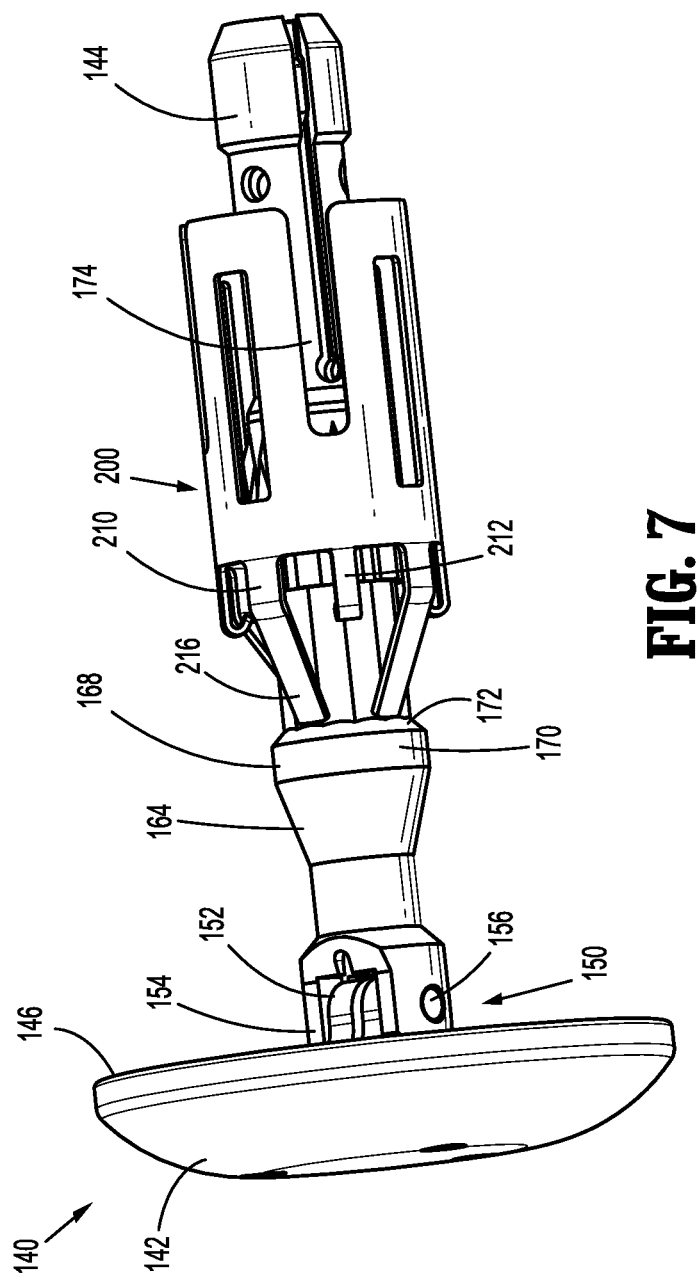
FIG. 7 is a perspective view of the anvil assembly of FIG. 5, illustrating the lockout sleeve engaged with a flange of the anvil shaft.

With reference now to FIGS. 5 and 7, once drive member 104 is retracted, knob 18 (FIG. 1) is actuated to un-approximate anvil assembly 140 relative to cartridge assembly 102. As anvil assembly 140 un-approximates relative to cartridge assembly 102, anvil shaft 144 slides distally relative to the legs 216 of lockout sleeve 200 such that the ends 216a of legs 216 slide along outer surface 168 of spring housing 164 and move inward to engage tapered portion 172 of flange 170 proximal of spring housing 164 due to the inward bias. Once legs 216 are engaged with the tapered portion 172 of spring housing 164, proximal movement of anvil assembly, and approximation of anvil assembly 140 relative to cartridge assembly 102, is inhibited by lockout sleeve 200. In this manner, the anvil assembly 140 is locked out after firing of the surgical stapling device 10 to inhibit further firing of circular stapler 10.

Figure 9:
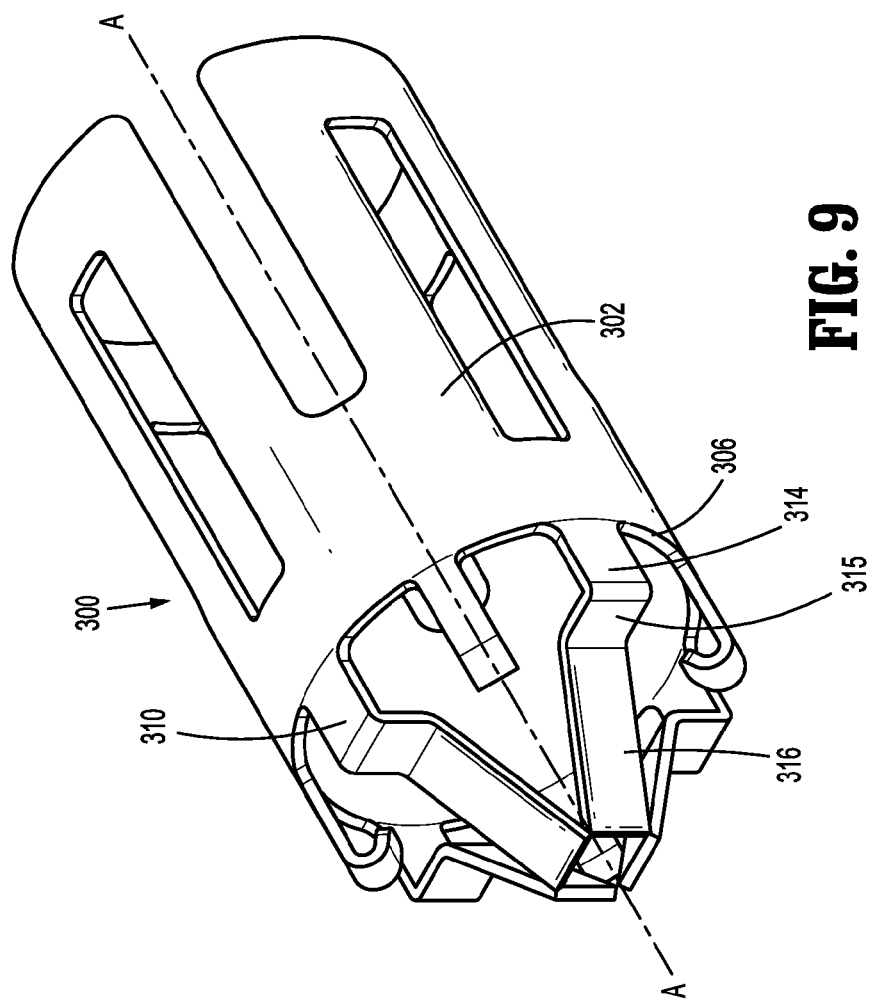
FIG. 9 is a perspective view of an alternate embodiment of the lockout sleeve of FIG. 2 including the tab of FIG. 8.
Figure 8:
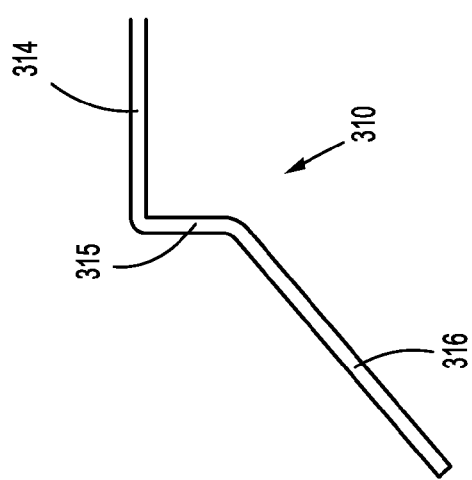
FIG. 8 is a side view of an alternate embodiment of a tab of the lockout sleeve of FIG. 2.

In another embodiment, referring now to FIGS. 8 and 9, a lockout sleeve 300 is disclosed that is similar to lockout sleeve 200 (FIG. 2). For brevity, only the differences between lockout sleeve 300 and lockout sleeve 200 (FIG. 2) will be discussed. Lockout sleeve 300 includes a plurality of tabs 310 extending from a distal end 306 of cylindrical housing 302. Each tab 310 includes a longitudinal portion 314 extending distally from the distal end 306 of cylindrical housing 302, a second portion 315 extending from longitudinal portion 314 substantially orthogonal to longitudinal portion 314 and longitudinal axis A-A, and a leg 316 extending distally from second portion 315 at an angle toward the longitudinal axis A-A. As with leg 216 (FIG. 2) above, leg 316 is biased inwards from longitudinal portion 314 and second portion 315 towards longitudinal axis A-A. Second portion 315 provides an additional inward biasing force on leg 316, as compared to the inward biasing force on leg 216 (FIG. 2) of lockout sleeve 200 (FIG. 2), when leg 316 is pressed outward by engagement with the inner cylindrical portion 110 (FIGS. 3-6A) of cartridge assembly 102 (FIGS. 3-6A) or the shaft 144 (FIGS. 3-6A) of anvil assembly 140 (FIGS. 3-6A). Lockout sleeve 300 otherwise functions in the manner describe above with regard to lockout sleeve 200 (FIG. 2).

It is contemplated that individual features of the above described embodiments may be combined without departing from the scope of the present disclosure. In addition, any of the above embodiments may alternatively include a powered actuation system as described above.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to the precise embodiments described herein, and that various other changes and modifications may be effected by one skilled in the art without departing from the scope or spirit of the present disclosure.

What is claimed is:

1. A surgical stapling device for joining tissue portions, comprising:
   a handle assembly;
   an elongate body extending from the handle assembly;
   a cartridge assembly supported on a distal end of the elongate body, the cartridge assembly including a staple cartridge containing a plurality of surgical staples in an annular array;
   an anvil assembly at a distal end of the surgical stapling device, the anvil assembly translatable relative to the cartridge assembly between a spaced position, where the anvil assembly is spaced from the cartridge assembly, and an approximated position, where the anvil assembly is in close cooperative alignment with the cartridge assembly for clamping tissue disposed therebetween; and
   a lockout sleeve slidably supported on the cartridge assembly and translatable relative to the cartridge assembly and the anvil assembly between a first position and a second position, the lockout sleeve configured to engage the anvil assembly and the cartridge assembly when the lockout sleeve is in the second position to inhibit translation of the anvil assembly relative to the cartridge assembly from the spaced position to the approximated position.

2. A surgical stapling device according to claim 1, wherein the lockout sleeve includes at least one tab extending therefrom and configured to engage the anvil assembly when the lockout sleeve is in the second position to inhibit proximal translation of the anvil assembly relative to the lockout sleeve.

3. A surgical stapling device according to claim 2, wherein the at least one tab includes a first portion substantially longitudinally aligned with the lockout sleeve and an inwardly biased leg extending from the first portion, the leg configured to engage a flange of the anvil assembly to inhibit proximal translation of the anvil assembly relative to the lockout sleeve.

4. A surgical stapling device according to claim 2, wherein the at least one tab includes a first portion substantially longitudinally aligned with the lockout sleeve, a second portion extending from the first portion substantially orthogonal to the first portion, and a leg extending from the second portion, the leg being inwardly biased relative to the first and second portions.

5. A surgical stapling device according to claim 2, wherein the at least one tab extends from a distal end of the lockout sleeve.

6. A surgical stapling device according to claim 2, wherein the cartridge assembly includes an inner cylindrical portion having at least one recess thereon, the at least one tab of the lockout sleeve being disposed against the at least one recess when the lockout sleeve is in the first position.

7. A surgical stapling device according to claim 1, wherein the lockout sleeve includes at least one hook extending therefrom and configured to engage the cartridge assembly when the lockout sleeve is in the second position to inhibit proximal translation of the lockout sleeve relative to the cartridge assembly.

8. A surgical stapling device according to claim 7, wherein the at least one hook is disposed adjacent a side wall of an inner cylindrical portion of the cartridge assembly when the lockout sleeve is in the first position and configured to snap over and engage an end of the inner cylindrical portion when the lockout sleeve is in the second position.

9. A surgical stapling device according to claim 8, wherein the at least one hook includes a first portion extending from the lockout sleeve and substantially aligned with the lockout sleeve and an arcuate portion extending from the first portion, the arcuate portion configured to snap over and engage the end of the inner cylindrical portion of the cartridge assembly when the lockout sleeve is in the second position.

10. A surgical stapling device according to claim 7, wherein the at least one hook extends from a distal end of the lockout sleeve.

11. A surgical stapling device according to claim 1, wherein the lockout sleeve includes a longitudinally extending slot configured for sliding reception of a tab of the cartridge assembly therein, the tab of the cartridge assembly configured to engage a proximal end of the slot when the lockout sleeve is in the second position to inhibit distal translation of the lockout sleeve relative to the cartridge assembly beyond the second position.

12. A surgical instrument according to claim 1, wherein the cartridge assembly includes a drive member operably coupled to the handle assembly, the drive member configured to engage the lockout sleeve to translate the lockout sleeve from the first position to the second position upon actuation of the handle assembly.

13. A surgical stapling device according to claim 1, wherein the cartridge assembly includes a knife pusher operably coupled to the handle assembly and configured to distally advance a knife blade to sever tissue disposed radially inward of the staple cartridge upon actuation of the handle assembly.

14. A surgical stapling device according to claim 1, wherein the cartridge assembly further includes a staple pusher operatively associated with the handle assembly and configured to drive the staples out of the cartridge assembly upon actuation of the handle assembly.

15. A surgical stapling device for joining tissue portions, comprising:
   a handle assembly;
   an elongate body extending from the handle assembly;
   a cartridge assembly supported on a distal end of the elongate body, the cartridge assembly including:
      a staple cartridge containing a plurality of surgical staples in an annular array;
      a staple pusher configured for advancement through the staple cartridge to eject the plurality of surgical staples from the staple cartridge;
      a knife assembly configured for advancement through the cartridge assembly to sever tissue;
      a drive member disposed within the cartridge assembly and in operative association with the handle assembly, the drive member configured to advance the staple pusher and the knife assembly upon actuation of the handle assembly;
   an anvil assembly at a distal end of the surgical stapling device, the anvil assembly translatable relative to the cartridge assembly between a spaced position, where the anvil assembly is spaced from the cartridge assembly, and an approximated position, where the anvil assembly is in close cooperative alignment with the cartridge assembly for clamping tissue disposed therebetween; and
   a lockout sleeve slidably supported on the cartridge assembly and translatable relative to the cartridge assembly and the anvil assembly between a first position and a second position, the lockout sleeve configured to engage the anvil assembly and the cartridge assembly when the lockout sleeve is in the second position to inhibit translation of the anvil assembly relative to the cartridge assembly from the spaced position to the approximated position.

* * * * *